United States Patent [19]

Wright, Jr. et al.

[11] Patent Number: 4,684,654
[45] Date of Patent: Aug. 4, 1987

[54] 3-HETEROALKYL-2,4-QUINZAOLINEDIONES

[75] Inventors: William B. Wright, Jr., Woodcliff Lake; Andrew S. Tomcufcik, Old Tappan, both of N.J.

[73] Assignee: American Cyanamid Company, Stamford, Conn.

[21] Appl. No.: 765,417

[22] Filed: Aug. 14, 1985

[51] Int. Cl.⁴ .................. A61K 31/505; C07D 403/06
[52] U.S. Cl. .................................... 514/259; 544/284
[58] Field of Search ........................ 544/284; 514/259

[56] References Cited

U.S. PATENT DOCUMENTS 3,274,194 9/1966 Hayao ................................. 544/284
4,166,117 8/1979 Vincent et al. .................... 544/284
4,276,295 6/1981 Ishikawa et al. ................... 544/284

OTHER PUBLICATIONS

Gadekar et al., "Chemical Abstracts", vol. 62, 1965, Col. 4028h.
Hayao et al., "Chemical Abstracts", vol. 63, 1965, col. 16347b.
Ueda, I. and Kato, M. *Chem. Abstracts* 203981t (vol. 102, p. 602) 1985 *Cardiovascular Diseases: New Trends in Surgical and Medical Aspects.*
Barnett, H. et al., eds., Elsevier/North-Holland Biomedical Press, pp. 137–150 (1981).
Villa, S. et al., *Lancet*(i) p. 1216 (1977).
Horrobin, D. F. et al., *Lancet* p. 479 (1977).
Ellis, E. F. et al., *Science,* 193 1135 (1976).
Helfant, R. H., *Amer. J. Cardiology,* 41 787 (1978).
Yarger, W. E. et al., *J. Clin. Invest.,* 65 400 (1980).
Moncada, S., *Br. J. Pharmacol.,* 76, 3 (1982).
Chan, P. S. and Cervoni, P., *Drug Development Research,* 7 341 (1986).
Nicolaou, K. C. et al., *Drugs of the Future,* 7, 331 (1982).
*Cardiovascular Pharmacology of the Prostaglandins,* Herman, A. G. et al., eds. Raven Press, New York, pp. 361–374 (1982).
Terashita, Z-I. et al., *Eur. J. Pharmacol.,* 53 49 (1978).

Sakai, K. et al., *J. Cardiovascular Pharmacol.,* 4 129 (1982).

Primary Examiner—Richard L. Raymond
Assistant Examiner—James H. Turnipseed
Attorney, Agent, or Firm—Susan H. Rauch

[57] ABSTRACT

Compounds of the formula:

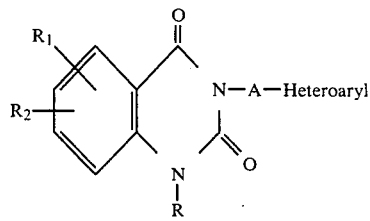

wherein A is a divalent moiety of the formula:

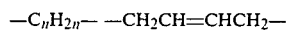

or

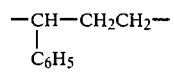

wherein n is an integer from 2–10, inclusive; R is hydrogen or alkyl having from one to four carbon atoms; $R_1$ and $R_2$ may be the same or different and may be selected from the group consisting of hydrogen, halogen, trifluoromethyl, alkoxy having from one to four carbon atoms, alkyl having from one to four carbon atoms, nitro and amino; wherein Heteroaryl is t,0012 wherein $R_3$ and $R_4$ may be selected from hydrogen, alkyl having from one to four carbon atoms, or phenyl; and X is CH or N, together with the pharmaceutically acceptable salts thereof, which act as thromboxane synthetase inhibitors and hypotensive agents; methods for their production and use.

20 Claims, No Drawings

3-HETEROALKYL-2,4-QUINZAOLINEDIONES

BRIEF SUMMARY OF THE INVENTION

This invention relates to new organic compounds and, more particularly, is concerned with novel 3-(ω-heteroalkyl)-2,4(1H,3H)-quinazolinediones which may be represented by the following structural formula:

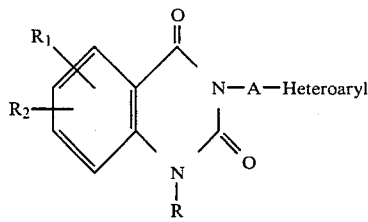

wherein A is a divalent moiety of the formula:

$$-C_nH_{2n}-\quad -CH_2CH=CHCH_2-$$

or

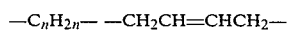

wherein n is an integer from 2–10, inclusive; R is hydrogen or alkyl having from one to four carbon atoms; $R_1$ and $R_2$ may be the same or different and may be selected from the group consisting of hydrogen, halogen, trifluoromethyl, alkoxy having from one to four carbon atoms, alkyl having from one to four carbon atoms, nitro and amino; wherein Heteroaryl is

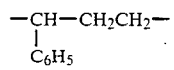

wherein $R_3$ and $R_4$ may be selected from hydrogen, alkyl having from one to four carbon atoms, or phenyl; and X is CH or N.

A preferred embodiment of the present invention may be represented by the following structural formula:

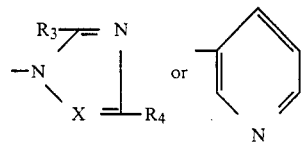

wherein R, $R_1$, $R_2$, $R_3$, $R_4$ and n are as hereinbefore defined.

The organic bases of this invention form non-toxic acid-addition salts with a variety of pharmacologically acceptable organic and inorganic salt-forming reagents. Thus, acid-addition salts, formed by admixture of the organic free base with one or more equivalents of an acid, suitably in a neutral solvent, are formed with such acids as sulfuric, phosphoric, hydrochloric, hydrobromic, maleic, sulfamic, citric, lactic, malic, succinic, tartaric, acetic, benzoic, fumaric, gluconic, ascorbic, and the like.

For purposes of this invention the free bases are equivalent to their non-toxic acid-addition salts.

The acid-addition salts of the organic bases of the present invention are, in general, relatively soluble in water, methanol and ethanol but relatively insoluble in non-polar organic solvents such as diethyl ether, benzene, toluene, and the like.

DETAILED DESCRIPTION OF THE INVENTION

The novel compounds of the present invention may be readily prepared as set forth in the following reaction scheme wherein heteroaryl, A, R, $R_1$ and $R_2$ are as hereinabove defined.

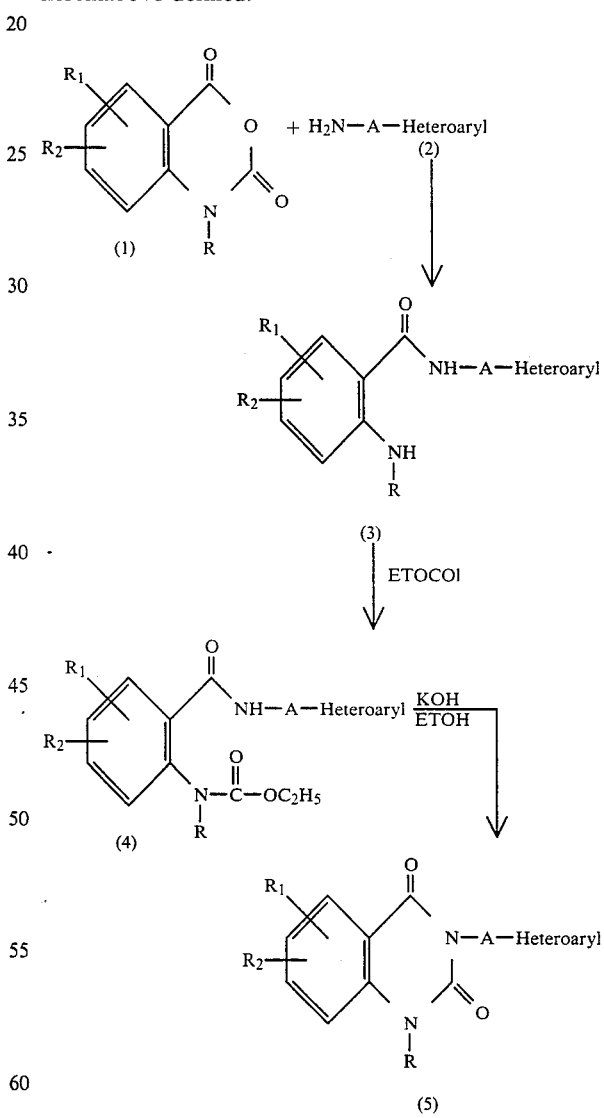

In accordance with this method, an appropriately substituted isatoic anhydride (1) is reacted with a heterocyclic alkylamine (2) in an inert solvent such as ethanol, toluene or dimethylsulfoxide at ambient temperature for 1–24 hours or with heating at 60°–120° C. for 15–120 minutes to provide the intermediate (3). Treatment of (3) with ethyl chloroformate, preferably at a temperature of 90°–105° C. for 1–2 hours results in (4), which is then cyclized by heating for 2–4 hours at reflux temperature with ethanolic potassium hydroxide. When the reaction mixture is concentrated and treated with an aqueous acid, such as acetic acid, to adjust the pH to 6–7, the desired product (5) is obtained.

The compounds of this invention inhibit thromboxane synthetase enzyme without interfering with other enzymes in the arachadonic acid cascade. Thus, these compounds are useful in the treatment of diseases characterized by an imbalance of thromboxane $A_2$/prostacyclin, such as ischemic heart disease, transient ischemic attack, thrombosis and migraine. Recent reviews have established the role of the thromboxane/prostacyclin balance in the vascular system [*Cardiovascular Diseases: New Trends in Surgical and Medical Aspects*, H. Barnett, P. Paoletti, E. Flamm and G. Brambilla, eds., Elsevier/North-Holland Biomedical Press, pp 137–150 (1981)]. Prostacyclin ($PGI_2$) is a potent vasodilator and platelet aggregation inhibitor, whereas thromboxane ($TXA_2$) is a powerful vasoconstrictor and inducer of platelet aggregation. $TXA_2$ synthesis is catalyzed by thromboxane synthetase enzyme located in, for example, blood platelets. When $TXA_2$ production is increased relative to $PGI_2$, platelet aggregation, thrombosis and vasopasm may occur [*Lancet* (i), 1216 (1977); *Lancet*, 479 (1977); *Science*, 193 1135 (1976); *Amer. J. Cardiology*, 41 787 (1978)]. $TXA_2$ synthetase inhibitors hve been shown to have anti-thrombotic action superior to that of aspirin [*J. Clin. Invest.*, 65 400 (1980); *Br. J. Pharmac.*, 76, 3, 1982].

The role of prostaglandins including $TXA_2$ and $PGI_2$ in ischemic heart patients has been reviewed [*Cardiovascular Pharmacology of the Prostaglandins*, A. G. Herman, P. M. Vanhoute, H. Denolin and A. Goosens, eds., Raven Press, New York, pp 361–374 (1981)]. Injection of $TXA_2$ into coronary arteries of guinea pigs and rabbits causes myocardial ischemia and subendocardial necrosis [*Drugs of Future*, 7, 331 (1982); *Eur. J. Pharmacol.*, 53 49(1978)]. Recent research has demonstrated the beneficial effects of $PGI_2$ and selective inhibition of thromboxane synthetase on ischemic myocardium in canines [*J. Cardiovascular Pharmacology*, 4, 129 (1982)]. Thus compounds which selectively inhibit thromboxane synthetase (and hence $TXA_2$) without adversely affecting $PGI_2$ are useful in the treatment of vacular diseases such as ischemia and migraine. In addition, inhibition of $TXA_2$ formation may effectively treat platelet aggregation and prevent thrombosis.

From Okamoto-Aoki spontaneously hypertensive rats (SHR) (Taconic Farms, Germantown, NY) between 19 and 24 weeks in age, under urethan anesthesia, 10 µl of arterial blood was collected in one ml of 3.2% sodium citrate in a polystyrene tube. The blood was diluted with 3 ml of cold saline and centrifuged at room temperature for 15 minutes at 460 xg. The platelet rich plasma (PRP) was separated. The platelets were isolated by centrifuging the PRP for 10 minutes at 1060 xg and were washed in 4 ml of cold oxygenated Krebs phosphate buffer, pH 7.4. The chilled platelets recovered from centrifuging at 800 xg for 10 minutes were resuspended in oxygenated Krebs phosphate buffer and diluted to contain $4.5-6.0 \times 10^4$ platelets/µl.

The inhibition of thromboxane (TX) formation was studied by determining the concentration of thromboxane $B_2$ ($TXB_2$), the stable hydrolysis product of $TXA_2$. Assay samples, prepared on ice, contained 200 µl platelet suspension, 50 µl saline, and 50 µl vehicle or drug under study at a concentration of $10^{-4}M$ (with OKY1581, UK-37248-01, 1-benzylimidazole, and/or indomethacin used as standards). The samples were incubated for 10 minutes at 37° C. in a metabolic shaker. The reaction was terminated by immersing the tubes in an ice bath and adding 50 µl of 0.5M citric acid. The samples were centrifuged for 10 minutes in a refrigerated centrigue and the supernatants thus obtained were decanted and stored at $-20°$ C. The $TXB_2$ content for each sample was determined by a direct radioimmunoassay (RIA) utilizing a $TXB_2$ specific RIA kit purchased from New England Nuclear, Boston, MA and results expressed as pg $TXB_2$ formed minute$^{-1}$ sample $^{-1}$, from which the percent inhibition of $TXB_2$ formation was calculated. The results of this test on representative compounds of this invention appear in Table I below.

TABLE I

| Compound | % Inhibition |
| --- | --- |
| 3-[3-(1H—Imidazol-1-yl)propyl]-2,4-(1H,3H)—quinazolinedione | 76 |
| 6-Bromo-3[4-(1H—Imidazol-1-yl)butyl]-2,4(1H,3H)—quinazolinedione | 98 |
| 3-[3-(1H—Imidazol-1-yl)propyl]-6-nitro-2,4(1H,3H)—quinazolinedione | 100 |
| 3-[5-(1H—Imidazol-1-yl)pentyl]-2,4-(1H,3H)—quinazolinedione | 98 |
| 3-[3-(4-Methyl-1H—imidazol-1-yl)-propyl]-2,4(1H,3H)—quinazolinedione | 98 |
| 3-[3-(1H—Imidazol-1-yl)butyl]-2,4-(1H,3H)—quinazolinedione | 100 |
| 3-[3-(1H—Imidazol-1-yl)-2-methyl-propyl]-2,4(1H,3H)—quinazolinedione | 100 |
| 3-[4-(3-Pyridinyl)butyl]-2,4(1H,3H)—quinazolinedione | 99 |
| 6-Chloro-[3-(4-methyl-1H—imidazol-1-yl)propyl]-2,4(1H,3H)—quinazolinedione | 99 |
| 6-Chloro-3-[4-(3-pyridinyl)butyl]-2,4-(1H,3H)—quinazolinedione | 100 |
| 6-Chloro-3-[3-(1H—imidazol-1-yl)-butyl]-2,4-(1H,3H)—quinazolinedione | 98 |
| 6-Chloro-3-[3-(1H—imidazol-1-yl)2-methylpropyl]-2,4(1H,3H)—quinazolinedione | 100 |
| 6-Bromo-3-[3-(1H—imidazol-1-yl)-propyl]-2,4(1H,3H)—quinazolinedione | 100 |
| 3-[4-(1H—Imidazol-1-yl)butyl]-2,4-(1H,3H)—quinazolinedione | 100 |
| 3-[3-(1H—Imidazol-1-yl)butyl]-6-methyl-2,4(1H,3H)—quinazolinedione | 88 |
| 6-Chloro-3-[4-(1H—imidazol-1-yl)-butyl]-2,4(1H,3H)—quinazolinedione | 93 |
| 6-Chloro-3-[3-(2-phenyl-1H—imidazol-1-yl)propyl]-2,4(1H,3H)—quinazolinedione | 52 |
| 6-Chloro-3-[4-(4-methyl-1H—imidazol-1-yl)butyl]-2,4(1H,3H)—quinazolinedione | 70 |
| 6-Chloro-3-[5-(1H—imidazol-1-yl)-pentyl]-2,4(1H,3H)—quinazolinedione | 63 |
| 6-Chloro-3-[3-(1H—imidazol-1-yl)-3-phenylpropyl]-2,4(1H,3H)—quinazolinedione | 93 |
| 7-Chloro-3-[4-(1H—imidazol-1-yl)-butyl]-2,4-(1H,3H)—quinazolinedione | 59 |
| 7-Chloro-3-[3-(1H—imidazol-1-yl)-butyl]2,4(1H,3H)—quinazolinedione | 51 |
| 7-Chloro-3-[3-(1H—imidazol-1-yl)-2-methylpropyl]-2,4(1H,3H)—quinazolinedione | 75 |
| 8-Chloro-3-[4-(1H—imidazol-1-yl)-butyl]-2,4(1H,3H)—quinazolinedione | 62 |
| 8-Chloro-3-[3-(1H—imidazol-1-yl)-butyl]-2,4(1H,3H)—quinazolinedione | 71 |
| 8-Chloro-3-[3-(1H—imidazol-1-yl)-2-methylpropyl]-2,4(1H,3H)—quinazolinedione | 71 |
| 6,8-Dichloro-3-[4-(1H—imidazol-1-yl)-butyl]-2,4(1H,3H)—quinazolinedione | 89 |

TABLE I-continued

| Compound | % Inhibition |
|---|---|
| 6,8-Dichloro-3-[3-(1H—imidazol-1-yl)-butyl]-2,4(1H,3H)—quinazolinedione | 67 |
| 6,8-Dichloro-3-[3-(1H—imidazol-1-yl)-2-methylpropyl]-2,4(1H,3H)—quinazolinedione | 86 |

The novel compounds of the present invention are also active hypotensive agents and were tested for hypotensive activity by the method of P. S. Chan and D. Poorvin, Clinical and Experimental Hypertension, 1 (6), 817–830 (1979). Male, 16 week old, spontaneously hypertensive rats of the Okamoto strain, from Taconic Farms, Germantown, New York having an average mean arterial blood pressure of 160±1.5 mm of mercury were used in the test. One to 3 rats were used per test compound. The rats were dosed by gavage with a test compound, suspended in 2% pre-boiled starch at a concentration of 50 mg/ml, at a dose of 100 mg/kg of body weight or less, with 0.9% sodium chloride loading at a dose of 25 ml/kg of body weight. A second identical dose of the test compound, without sodium chloride loading is given 24 hours later. At 28 hours after the initial dose, the mean arterial blood pressure (MABP) is measured by the method of Chan and Poorvin vide supra. The procedure is repeated in a second and third rat when necessary.

The results of this test on representative compounds of the present invention appear in Table II below.

TABLE II

| Compound | MABP/mm Hg (no. of rats) |
|---|---|
| 3-[3-(1H—Imidazol-1-yl)propyl]-2,4(1H,3H)—quinazolinedione | 131(3) |
| 3-[4-(1H—Imidazol-1-yl)butyl]-2,4(1H,3H)—quinazolinedione | 108(2) |
| 6-Bromo-3-[4-(1H—imidazol-1-yl)butyl]-2,4(1H,3H)—quinazolinedione | 107(2) |
| 3-[3-(1H—Imidazol-1-yl)butyl]-6-methyl-2,4(1H,3H)—quinazolinedione | 111(2) |
| 3-[5-(1H—Imidazol-1-yl)pentyl]-2,4(1H,3H)—quinazolinedione | 104(2) |
| 3-[3-(4-Methyl-1H—imidazol-1-yl)propyl]-2,4(1H,3H)—quinazolinedione | 135(3) |
| 3-[3-(1H—Imidazol-1-yl)butyl]-2,4(1H,3H)—quinazolinedione | 121(3) |
| 3-[3-(1H—Imidazol-1-yl)-2-methylpropyl]-2,4(1H,3H)—quinazolinedione | 112(2) |
| 6-Chloro-3-[4-(1H—imidazol-1-yl)butyl]-2,4(1H,3H)—quinazolinedione | 106(2) |
| 6-Chloro-3-[3-(4-methyl-1H—imidazol-1-yl)propyl]-2,4(1H,3H)—quinazolinedione | 125(3) |
| 6-Chloro-3-[4-(4-methyl-1H—imidazol-1-yl)butyl]-2,4(1H,3H)—quinazolinedione | 118(2) |
| 6-Chloro-3-[3-(1H—imidazol-1-yl)butyl]-2,4(1H,3H)—quinazolinedione | 113(2) |
| 6-Chloro-3-[3-(1H—imidazol-1-yl)-2-methylpropyl]-2,4(1H,3H)—quinazolinedione | 126(3) |
| 7-Chloro-3-[4-(1H—imidazol-1-yl)butyl]-2,4(1H,3H)—quinazolinedione | 102(2) |
| 7-Chloro-3-[3-(1H—imidazol-1-yl)butyl]-2,4(1H,3H)—quinazolinedione | 128(2) |
| 7-Chloro-3-[3-(1H—imidazol-1-yl)-2-methylpropyl]-2,4(1H,3H)—quinazolinedione | 121(2) |
| 8-Chloro-3-[4-(1H—imidazol-1-yl)butyl]-2,4(1H,3H)—quinazolinedione | 85(2) |
| 8-Chloro-3-[3-(1H—imidazol-1-yl)butyl]-2,4(1H,3H)—quinazolinedione | 112(2) |
| 7,8-Dimethyl-3-[4-(1H—imidazol-1-yl)butyl]-2,4(1H,3H)—quinazolinedione | 104(2) |

The novel compounds of the present invention have been found to be highly useful for inhibiting thromboxane synthetase and/or lowering elevated blood pressure in mammals when administered in amounts ranging from about 0.1 mg to about 20.0 mg/kg of body weight per day. A preferred dosage regimen for optimum results would be from about 0.5 mg to about 10.0 mg/kg of body weight per day. Such dosage units are employed that a total of from about 35 to about 700 mg of active compound for a subject of about 70 kg of body weight are administered in a 24 hour period. This dosage regimen may be adjusted to provide the optimum therapeutic response. For example, several divided doses may be administered daily or the dose may be proportionally reduced as indicated by the exigencies of the therapeutic situation. The compounds of this invention are preferably administered orally but may be administered in any convenient manner such as by the intravenous, intramuscular, or subcutaneous routes.

Compositions according to the present invention having the desired clarity, stability and adaptability for parenteral use are obtained by dissolving from 0.10% to 10.0% by weight of active compound in a vehicle consisting of a polyhydric aliphatic alcohol or mixtures thereof. Especially satisfactory are glycerin, propylene glycol, and polyethylene glycols. The polyethylene glycols consist of a mixture of non-volatile, normally liquid, polyethylene glycols which are soluble in both water and organic liquids and which have a molecular weight of from about 200 to 1500. Although the amount of active compound dissolved in the above vehicle may vary from 0.10% to 10.0% by weight, it is preferred that the amount of active compound employed be from about 3.0 to about 9.0% by weight. Although various mixtures of the aforementioned non-volatile polyethylene glycols may be employed, it is preferred to use a mixture having an average molecular weight of from about 200 to about 400.

In addition to the active compound, the parenteral solutions may also contain various preservatives which may be used to prevent bacterial and fungal contamination. The preservatives which may be used for these purposes are, for example, myristyl-gamma-picolinium chloride, benzalkonium chloride, phenethyl alcohol, p-chlorophenyl-α-glycerol ether, methyl and propyl parabens, and thimerosal. As a practical matter, it is also convenient to employ antioxidants. Suitable antioxidants include, for example, sodium bisulfite, sodium metabisulfite, and sodium formaldehyde sulfoxylate. Generally, from about 0.05 to about 0.2% concentrations of antioxidant are employed.

For intramuscular injection, the preferred concentration of active compound is 0.25 to 0.50 mg/ml of the finished compositions. The novel compounds of the present invention are equally adapted to intravenous administration when diluted with water or diluents employed in intravenous therapy such as isotonic glucose in appropriate quantities. For intravenous use, initial concentrations down to about 0.05 to 0.25 mg/ml of active ingredient are satisfactory.

The active compounds of the present invention may be orally administered, for example, with an inert diluent or with an assimilable edible carrier, or they may be enclosed in hard or soft shell gelatin capsules, or they may be compressed into tablets, or they may be incorporated directly with the food of the diet. For oral therapeutic administration, the active compounds may be incorporated with excipients and used in the form of tablets, troches, capsules, elixirs, suspensions, syrups, wafers, and the like. Such compositions and preparations should contain at least 0.1% of active compound. The percentage of the compositions and preparations may, of course, be varied and may conveniently be between about 2% and about 60% of the weight of the unit. The amount of active compound in such therapeutically useful compositions is such that a suitable dosage will be obtained.

The tablets, troches, pills, capsules and the like may also contain the following: A binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain, in addition to materials of the above type, a liquid carrier such as a fatty oil. Various other materials may be present as coatings or to otherwise modify the physical form of the dosage unit. For instance, tablets, pills or capsules may be coated with shellac, sugar or both. A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed.

The following specific examples illustrate the preparation of the compounds of the present invention.

EXAMPLE 1

2-Amino-N-[4-(1H-imidazol-1-yl)butyl]benzamide

A mixture of 1.63 g of isatoic anhydride, 1.39 g of 1H-imidazole-1-butanamine and 25 ml of ethanol was stirred at room temperature for 22 hours. The reaction mixture was concentrated and the residue was dissolved in ethyl acetate and cooled. The desired product was isolated by filtration, mp 91°–93° C.

Following the procedure of this example and using the appropriate isatoic anhydride derivative, the products of examples 2–4 were obtained as set forth in Table III below.

TABLE III

| Ex. | Isatoic Anhydride | Product | mp °C. |
|---|---|---|---|
| 2 | 5-bromo | 2-Amino-5-bromo-N—[4-(1-H—imidazole-1-yl)butyl]benzamide | 108–110 |
| 3 | 5-nitro | 2-Amino-N—[4-(1H—imidazol-1-yl)butyl]-5-nitrobenzamide | 179–182 |
| 4 | 5-methyl | 2-Amino-N—[4-(1H—imidazol-1-yl)butyl]-5-methylbenzamide | 82–84 |

EXAMPLE 5

2-Amino-N-[3-(1H-imidazole-1-yl)propyl]benzamide

A mixture of 2.93 g of isatoic anhydride, 2.50 g of 1H-imidazole-propanamine and 30 ml of toluene was heated at 90° C. for 45 minutes and cooled. The toluene layer was decanted and the residue was dissolved in methylene chloride, washed with dilute sodium hydroxide solution, water and dried over magnesium sulfate. The organic layer was concentrated to obtain the desired product, mp 107°–110° C.

EXAMPLE 6

2-Amino-N-[3-(1H-imidazol-1-yl)propyl]-5-nitrobenzamide

A mixture of 8.32 g of 5-nitro isatoic anhydride, 5.0 g of 1H-imidazole-1-propanamine and 80 ml of ethanol was stirred at room temperature for 20 hours and concentrated. The residue was washed onto a filter with ethanol and washed with ether. Recrystallization from ethanol resulted in the pure product, mp 168°–170° C.

Following the procedure of this example and using the appropriate isatoic anhydride and amine, the products of Examples 7–8 were obtained as set forth in Table IV below.

TABLE IV

| Ex. | Isatoic Anhydride | Amine | Product | mp °C. |
|---|---|---|---|---|
| 7 | 5-chloro | 1H—Imidazole-1-propanamine | 2-Amino-5-chloro-N—[3-(1H—imidazol-1-yl)propyl]benzamide | 155–157 |
| 8 | 5-methyl | 3-(1H—Imidazol-1-yl)butanamine | 2-Amino-N—[3-(1H—imidazol-1-yl)butyl]-5-methylbenzamide | 128–130 |

EXAMPLE 9

1H-Imidazole-1-decanamine

A mixture of 100.0 g of 1,10-dibromodecane and 50.0 g of 1H-isoindole-1,3(2H)-dione, potassium salt in 500 ml of N,N-dimethylformamide was stirred and heated on a steam bath for eight hours. The reaction mixture was clarified while hot with activated charcoal, then filtered. The material on the filter was washed with 100 ml of N,N-dimethylformamide. The filtrate and wash were combined and taken to dryness in vacuo. The residue was triturated with 100 ml of hexane. The insoluble product was collected, washed with 50 ml of hexane, then air dried and gave 81.0 g of 2-(10-bromodecyl)-1H-isoindole-1,3(2H)-dione.

A 99.0 g amount of 2-(10-bromodecyl)-1H-isoindole-1,3(2H)-dione (prepared as described above) was dissolved in 300 ml of warm N,N-dimethylformamide with stirring. This solution was added to a stirred solution of 1H-imidazole, sodium salt (prepared by stirring a mixture of 20 g of imidazole and 14.0 g 50% sodium hydride in 500 ml of N,N-dimethylformamide at room temperature for 48 hours). The resulting mixture was heated on a steam bath for 14 hours, then taken to dryness in vacuo. The residue was partitioned between 500 ml of dichloromethane and 250 ml of water. The organic layer was washed with 250 ml of water, dried over magnesium sulfate and filter. The filtrate was evaporated in vacuo and gave 85.4 g of 2[10-(1H-imidazol-1-yl)decyl]-1H-isoindole-1,3(2H)dione as an oil which solidified on standing at room temperature.

The above product (85.4 g) was dissolved in one liter of hot ethanol, 17.0 ml of hydrazine hydrate was added and the mixture was heated at gentle reflux for 25 hours. The reaction mixture was filtered hot. The precipitate collected was extracted successively with 300 ml of hot hydrochloric acid, 300 ml of hot water, then 300 ml of water. The preceding filtrate was taken to dryness in vacuo and the resulting residue was mixed with the combined acid-water extracts (900 ml) and heated to the boil. The mixture was filtered while hot and the material on the filter was washed with 300 ml of hot water. The above filtrate and water wash were combined, heated to a boil, treated with activated charcoal and filtered. The filtrate was evaporated to dryness in vacuo. The resulting waxy residue was partitioned between 300 ml of methylene chloride and 200 ml of 5N sodium hydroxide. The organic layer was dried over magnesium sulfate and filtered. The filtrate was evaporated in vacuo and gave 38.1 g of the product of the example as an oil.

EXAMPLE 10

3-[3-(1H-Imidazol-1-yl)propyl]-2,4-(1H,3H)-quinazolinedione

A mixture of 4.0 g of 2-amino-N-[3-(1H-imidazol-1-yl)propyl]benzamide and 15 ml of ethyl chloroformate was heated in an oil bath at 95°–105° C. for 1.5 hours, dissolved in 50 ml of ethanol, and concentrated. The residue was mixed with 100 ml of ethanol and 3.2 g of potassium hydroxide, heated at reflux temperature for 3 hours and concentrated. The residue was dissolved in water and acidified with acetic acid to pH 6–7. The white precipitate was separated by filtration and recrystallized from ethanol. The desired product melted at 197°–200° C.

Following the procedure of this example and using the appropriate diamine precursor the products of Examples 11–17 were obtained as set forth in Table V below.

EXAMPLE 18

3-[5-(1H-Imidazol-1-yl)pentyl]-2,4(1H,3H)-quinazolinedione

A mixture of 1.53 g of 1H-imidazole-1-pentanamine, 1.63 g of isatoic anhydride and 15 ml at ethanol was stirred for 20 hours and concentrated. The viscous residue was mixed with 10 ml of ethyl chloroformate and heated for 1.5 hours in an oil bath at 95° C. The mixture was dissolved in ethanol, reconcentrated, mixed with 2.0 g of potassium hydroxide and 50 ml of ethanol and heated at reflux temperature for 3 hours. The reaction mixture was concentrated, dissolved in water and treated with acetic acid to pH 6–7. The insoluble material was collected by filtration and recrystallized from ethanol to obtain the desired product, mp 160°–162° C.

When the procedure of this example was followed using isatoic anhydride and the appropriate diamine, the products of examples 19–23 were obtained as set forth in Table VI below.

TABLE VI

| Ex. | Diamine Precusor | Product | mp °C. |
|---|---|---|---|
| 19 | (4-Methyl-1H—imidazol-1-yl)-1-propanamine | 3-[3-(4-Methyl-1H-imidazol-1-yl)propyl]-2,4(1H,3H)—quinazolinedione | 192–195 |
| 20 | 3-(1H—Imidazol-1-yl)-butanamine | 3-[3-(1H—Imidazol-1-yl)butyl]-2,4(1H,3H)—quinazolinedione | 130–133 |
| 21 | 3-(1H—Imidazol-1-yl)-2-methylpropanamine | 3-[3-(1H—Imidazol-1-yl)-2-methylpropyl]-2,4(1H,3H)—quinazolinedione | 206–208 |
| 22 | 4-(3-Pyridinyl)butanamine | 3-[4-(Pyridinyl)butyl]-2,4(1H,3H)—quinazolinedione | 141–143 |
| 23 | 6-(1H—Imidazol-1-yl)-hexanamine | 3-[6-(1H—Imidazol-1-yl)hexyl]-2,4(1H,3H)—quinazolinedione | 135–137 |

EXAMPLE 24

6-Chloro-3-[4-(1H-imidazol-1-yl)butyl]-2,4(1H,3H)-quinazolinedione

A mixture of 1.98 g of 5-chloroisatoic anhydride, 1.39 g of 1H-imidazole-1-butanamine, and 20 ml of ethanol was allowed to stand at room temperature for 20 hours and concentrated. The residue and 10 ml of ethyl chloroformate were heated at 90°–105° C. for 2 hours, dissolved in ethanol and concentrated. A mixture of the residue, 2.0 g of potassium hydroxide and 25 ml of ethanol was heated at reflux temperature for 3 hours and concentrated. Water and acetic acid were added to a pH of 6–7. The solid was separated by filtration and recrystallized from ethanol. The product melted at 220°–222° C.

When the procedure of example 24 was followed using 5-chloroisatoic anhydride and the appropriate

TABLE V

| Ex. | Diamine Precursor | Product | mp °C. |
|---|---|---|---|
| 11 | Example 1 | 3-[4-(1H—Imidazol-1-yl)butyl]-2,4(1H,3H)—quinazolinedione | 177–179 |
| 12 | Example 2 | 6-Bromo-3-[4-(1H—imidazol-1-yl)butyl]-2,4(1H,3H)—quinazolinedione | 227–229 |
| 13 | Example 3 | 3-[4-(1H—Imidazol-1-yl)butyl]-6-nitro-2,4(1H,3H)—quinazolinedione | 245–248 |
| 14 | Example 4 | 3-[4-(1H—Imidazol-1-yl)butyl]-6-methyl-2,4(1H,3H)—quinazolinedione | 189–191 |
| 15 | Example 6 | 3-[3-(1H—Imidazol-1-yl)propyl]-6-nitro-2,4(1H,3H)—quinazolinedione | 268–270 |
| 16 | Example 7 | 6-Chloro-3-[3-(1H—imidazol-1-yl)propyl]-2,4(1H,3H)—quinazolinedione | 222–224 |
| 17 | Example 8 | 3-[3-(1H—Imidazol-1-yl)butyl]-6-methyl-2,4(1H,3H)—quinazolinedione | 195–196 | diamine precursor the products of examples 25-36 were obtained as described in Table VII.

TABLE VII

| Ex. | Diamine Precursor | Product | mp °C. |
|---|---|---|---|
| 25 | 3-(2-Methyl-1H—imidazol-1-yl)-1-propanamine | 6-Chloro-3-[3-(2-methyl-1H—imidazol-1-yl)-propyl-2,4(1H,3H)—quinazolinedione | 221-223 |
| 26 | 3-(4-Methyl-1H—imidazol-1-yl)-1-propanamine | 6-Chloro-3-[3-(4-methyl-1H—imidazol-1-yl)-propyl]-2,4(1H,3H)—quinazolinedione | 206-210 |
| 27 | 3-(2-Phenyl-1H—imidazol-1-yl)-1-propanamine | 6-Chloro-3-[3-(2-phenyl-1H—imidazol-1-yl)propyl]-2,4(1H,3H)—quinazolinedione | 224-226 |
| 28 | 3-(4-Methyl-1H—imidazol-1-yl)-1-butanamine | 6-Chloro-3-[4-methyl-1H—imidazol-1-yl)butyl]-2,4(1H,3H)—quinazolinedione | 186-189 |
| 29 | 4-(3-Pyridinyl)butanamine | 6-Chloro-3-[4-(3-pyridinyl)butyl]-2,4(1H,3H)—quinazolinedione | 228-231 |
| 30 | 3-(1H—Imidazol-1-yl)-butanamine | 6-Chloro-3-[3-(1H—imidazol-1-yl)-butyl]-2,4(1H,3H)—quinazolinedione | 178-180 |
| 31 | 3-(1H—Imidazol-1-yl)-2-methylpropylamine | 6-Chloro-3-[3-(1H—imidazol-1-yl)-2-methylpropyl]-2,4(1H,3H)—quinazolinedione | 208-210 |
| 32 | 1H—Imidazole-1-pentanamine | 6-Chloro-3-[5-(1H—imidazol-1-yl)pentyl]-2,4(1H,3H)—quinazolinedione | 170-172 |
| 33 | 1H—Imidazole-1-hexanamine | 6-Chloro-3-[6-(1H—imidazol-1-yl)hexyl]-2,4(1H,3H)—quinazolinedione | 200-203 |
| 34 | 1H—Imidazole-1-octanamine | 6-Chloro-3-[8-(1H—imidazol-1-yl)-octyl]-2,4(1H,3H)—quinazolinedione | 120-135 |
| 35 | 1H—Imidazole-1-decanamine | 6-Chloro-3-[10-(1H—imidazol-1-yl]decyl]-2,4(1H,3H)—quinazolinedione | 94-96 |
| 36 | 3-(1H—Imidazol-1-yl)-3-phenylpropanamine | 6-Chloro-3-[3-(1H—imidazol-1-yl)-3-phenylpropyl]-2,4(1H,3H)—quinazolinedione | 287-289 |

EXAMPLE 37

6-Chloro-3-[4-(1H-imidazol-1-yl)-2-butenyl]-2,4(1H,3H)-quinazolinedione

The above compound is obtained when 5-chloroisatoic anhydride is reacted with 4-(1H-imidazol-1-yl)-2-butenamine by the procedure of example 24.

EXAMPLE 38

6-Fluoro-3-[4-(1H-imidazol-1-yl)butyl]-2,4(1H,3H)-quinazolinedione

When 5-fluoroisatoic anhydride and 1H-imidazole 1-butanamine are reacted by the procedure of example 24, this compound is obtained.

EXAMPLE 39

3-[4-(1H-Imidazol-1-yl)butyl-2,4(1H,3H)-6-methoxy-quinazolinedione

This compound is obtained when 5-methoxyisatoic anhydride is substituted for 5-chloroisatoic anhydride in the procedure of example 24.

EXAMPLE 40

7-Chloro-3-[4-(1H-imidazole-1-yl)butyl]-2,4(1H,3H)-quinazolinedione

A mixture of 1.39 g of 1H-imidazole-1-butanamine, 1.98 g of 4-chloroisatoic anhydride and 20 ml of ethanol was allowed to stir at room temperature for 20 hours and concentrated. The residue and 10 ml of ethyl chloroformate were heated at 90°-105° C. for 2 hours, dissolved in ethanol and concentrated. The residue, 25 ml of ethanol and 2.0 g of potassium hydroxide were heated at reflux temperature for 3 hours, concentrated, an treated with water and acetic acid to a pH of 6-7. The solid material was isolated by filtration and recrystallized from ethanol to obtain the desires product, mp 196°-198° C.

The procedure of the above example was followed using the appropriate isatoic anhydride and diamine to obtain the products of example 41-54 as set forth in Table VIII.

TABLE VIII

| Ex. | Isatoic Anhydride | Diamine | Product | mp °C. |
|---|---|---|---|---|
| 41 | 4-Chloro | 3-(1H—Imidazol-1-yl)butanamine | 7-Chloro-3-[3-(1H—imidazol-1-yl)butyl]-2,4(1H,3H)—quinazolinedione | 243-245 |
| 42 | 4-Chloro | 3-(1H—Imidazol-1-2-methylpropan-amine | 7-Chloro-3-[3-(1H—imidazol-1-yl)-2-methylpropyl]-2,4(1H,3H)—quinazolinedione | 200-203 |
| 43 | 3-Chloro | 1H—Imidazole-1-butanamine | 8-Chloro-3-[4-(1H—imidazol-1-yl)butyl]-2,4(1H,3H)—quinazolinedione | 155-157 |
| 44 | 3-Chloro | 3-(1H—Imidazol-1-yl)butanamine | 8-Chloro-3-[3-(1H—imidazol-1-yl)butyl]-2,4(1H,3H)—quinazolinedione | 219-221 |
| 45 | 3-Chloro | 3-(1H—Imidazol-1-yl)-2-methyl-propanamine | 8-Chloro-3-[-3-(1H—imidazol-1-yl)-2-methylpropyl]-2,4(1H,3H)—quinazolinedione | 163-165 |
| 46 | 3,5-Dichloro | 1H—Imidazole-1-butanamine | 6,8-Dichloro-3-[4-(1H—imidazol-1-yl)-butyl]-2,4(1H,3H)—quinazolinedione | 215-217 |
| 47 | 3,5-Dichloro | 3-(1H—Imidazol-1-yl)butanamine | 6,8-Dichloro-3-[3-(1H—imidazol-1-yl)-butyl]-2,4(1H,3H)—quinazolinedione | 222-224 |
| 48 | 3,5-Dichloro | 3-(1H—Imidazol-1-yl)-2-methyl-propanamine | 6,8-Dichloro-3-[3-(1H—imidazol-1-yl)-2-methylpropyl]-2,4(1H,3H)—quinazolinedione | 255-257 |
| 49 | 5-Methyl | 3-(1H—Imidazol-1-yl)-2-methyl- | 3-[3-(1H—Imidazol-1-yl)-2-methylpropyl]-6-methyl-2,4(1H,3H)—quinazolinedione| | 193-195 |

TABLE VIII-continued

| Ex. | Isatoic Anhydride | Diamine | Product | mp °C. |
|---|---|---|---|---|
| 50 | 3,4-Dimethyl | 1H—Imidazole-1-propanamine / 1H—Imidazole-1-butanamine | 7,8-Dimethyl-3-[4-(1H—imidazol-1-yl)butyl]-2,4(1H,3H)—quinazolinedione | 197–199 |
| 51 | 5-Bromo | 1H—Imidazole-1-propanamine | 6-Bromo-3-[3-(1H—imidazol-1-yl)propyl]-2,4(1H,3H)—quinazolinedione | 257–260 |
| 52 | 3-Methyl-5-chloro | 1H—Imidazole-1-propanamine | 6-Chloro-3-[3-(1H—imidazol-1-yl)propyl]-8-methyl-2,4(1H,3H)—quinazolinedione, hydrochloride | 297–300 |
| 53 | 5-Methyl | 1H—Imidazole-1-propanamine | 3-[3-(1H—Imidazol-1-yl)propyl]-6-methyl-2,4(1H,3H)—quinazolinedione | 218–220 |
| 54 | 4-Chloro | 1H—Imidazole-1-propanamine | 7-Chloro-3-[3-(1H—imidazol-1-yl)propyl]-2,4(1H,3H)—quinazolinedione | 225–227 |

EXAMPLE 55

3-[4-(1H-Imidazol-1-yl)butyl]-6-trifluoromethyl-2,4(1H,3H)-quinazolinedione

When 5-trifluoromethylisatoic anhydride is substituted for 4-chloroisatoic anhydride in the procedure of example 40, the above compound is obtained.

EXAMPLE 56

3-[3-(1H-Triazol-1-yl)propyl]-2,4(1H,3H)-quinazolinedione

A mixture of 1.25 g of 1H-1,2,4-triazole-1-propanamine, 1.63 g of isatoic anhydride and 25 ml of ethanol is stirred at room temperature for 20 hours and concentrated. The residue and 10 ml of ethyl chloroformate are heated at 90°–105° for 2 hours, dissolved in ethanol and concentrated. The reaction mixture is heated at reflux temperature for 3 hours with 25 ml ethanol and 2.0 g of potassium hydroxide, concentrated, and treated with water and acetic acid to a pH of 6–7. The desired compound is isolated by filtration.

EXAMPLE 57

6-Amino-3-[4-(1H-imidazol-1-yl)butyl]-2,4(1H,3H)-quinazolinedione

A mixture of 2.0 g of 3-[4-(1H-imidazol-1-yl)butyl]-6-nitro-2,4(1H,3H)-quinazolinedione, 1.0 g of 10% palladium-on-carbon catalyst and 200 ml of ethanol is shaken in a Parr hydrogenater under 45 pounds of hydrogen pressure until the hydrogen uptake is complete. The reaction mixture is heated to the boil and the catalyst is filtered off. The ethanolic solution is concentrated to a low volume and the desired product is recovered by filtration.

EXAMPLE 58

7-Chloro-3-[3-(1H-imidazol-1-yl)-2-methylpropyl]-1-methyl-2,4(1H,3H)-quinazolinedione A mixture of 2.12 g of 4-chloro-N-methylisatoic anhydride, 1.39 g of 3-(1H-imidazol-1-yl)-2-methylpropanamine and 20 ml of ethanol was stirred at room temperature for 20 hours and concentrated. Ethyl chloroformate (10 ml) was added and the mixture was heated in an oil bath at 90°–105° C. for 2 hours, dissolved in ethanol and concentrated. Ethanol (25 ml) and 2.0 g of potassium hydroxide was added and the mixture was heated at reflux for 3 hours and concentrated. Water was added, and the pH was adjusted to 6–7 with acetic acid. The product was extracted into methylene chloride. Concentration and recrystallization from ethyl acetate resulted in the desired product, mp 206°–209° C.

EXAMPLE 59

1-Ethyl-3-[3-(1H-imidazol-1-yl)propyl]-2,4(1H,3H)-quinazolinedione

The above compound, mp 110°–112° C., was obtained when N-ethylisatoic anhydride was reacted with 1H-imidazole-1-propanamine by the procedure of Example 58.

What is claimed is:

1. A compound selected from the group consisting of those of the formula:

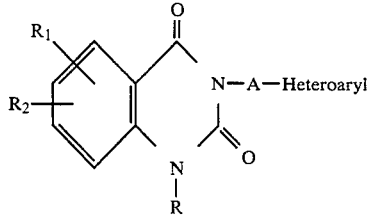

wherein A is a divalent moiety of the formula:

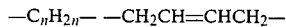

or

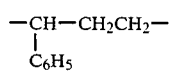

wherein n is an integer from 2–10, inclusive; R is hydrogen or alkyl having from one to four carbon atoms; $R_1$ and $R_2$ may be the same or different and may be selected from the group consisting of hydrogen, halogen, trifluoromethyl, alkoxy having from one to four carbon atoms, alkyl having from one to four carbon atoms, nitro and amino; wherein Heteroaryl is

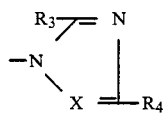

wherein $R_3$ and $R_4$ may be selected from hydrogen, alkyl having from one to four carbon atoms, or phenyl; and X is CH or N, together with the pharmaceutically acceptable salts thereof.

2. A compound according to claim 1, wherein A is $-C_nH_{2n}-$, Heteroaryl is

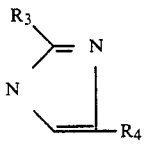

and each of $R_1$ and $R_2$ may be hydrogen or halogen,

3. A compound according to claim 2, wherein n is 4, $R_1$ is H and $R_2$ is Cl.

4. A compound according to claim 3, which is selected from the group consisting of: 6-chloro-3-[3-(1H-imidazol-1-yl)butyl]-2,4(1H,3H)-quinazolinedioine; 6-chloro-3-[4-(1H-imidazol-1-yl)butyl]-2,4(1H,3H)-quinazolinedione; 6-chloro-3-[4-(4-methyl-1H-imidazol-1-yl)butyl]-2,4(1H,3H)-quinazolinedione; 7-chloro-3-[4-(1H-imidazol-1-yl)butyl]-2,4(1H,3H)-quinazolinedione; 8-chloro-3-[4-(1H-imidazol-1-yl)butyl]-2,4(1H,3H)-quinazolinedione; and 8-chloro-3-[3-(1H-imidazol-1-yl)butyl]-2,4(1H,3H)-quinazolinedione.

5. A compound according to claim 1 which is 6-bromo-3-[4-(1H-imidazol-1-yl)butyl]-2,4(1H,3H)-quinazolinedione.

6. A compound according to claim 1 which is 3-5-(1H-imidazol-1-yl)pentyl]-2,4(1H,3H)-quinazolinedione.

7. A compound according to claim 1 which is 3-[3-(1H-imidazol-1-yl)butyl]-2,4(1H,3H)-quinazolinedione.

8. A compound according to claim 1 which is 3-[3-(1H-imidazol-1-yl)-2-methylpropyl]-2,4(1H,3H)-quinazolinedione.

9. A compound according to claim 1 which is 6-chloro-3-[3-(4-methyl-1H-imidazol-1-yl)propyl]-2,4(1H,3H)-quinazolinedione.

10. A compound according to claim 1 which is 6-bromo-3-[3-(1H-imidazol-1-yl)propyl]-2,4(1H,3H)-quinazolinedione.

11. A compound according to claim 1 which is 3-[4-(1H-imidazol-1-yl)butyl]-2,4(1H,3H)-quinazolinedione.

12. A compound according to claim 1 which is 3-[3-(1H-imidazol-1-yl)butyl]-6-methyl-2,4(1H,3H)-quinazolinedione.

13. A compound according to claim 1 which is 3-[4-(1H-imidazol-1-yl)butyl]-7,8-dimethyl-2,4(1H,3H)quinazolinedione.

14. A method of inhibiting thromboxane synthetase enzyme in a mammal in need thereof which comprises administering internally to said mammal a pharmacologically effective amount of a compound selected from those of the formula:

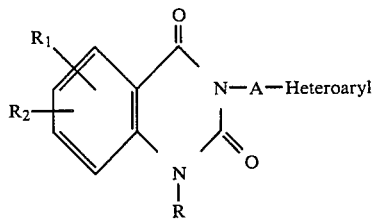

wherein A is a divalent moiety of the formula:

$-C_nH_{2n}-$  $-CH_2CH=CHCH_2-$ or or $$-CH-CH_2CH_2-$$
$$\phantom{-}|\phantom{-}$$
$$\phantom{-}C_6H_5$$

wherein n is an integer from 2-10, inclusive; R is hydrogen or alkyl having from one to four carbon atoms; $R_1$ and $R_2$ may be the same or different and may be selected from the group consisting of hydrogen, halogen, trifluoromethyl, alkoxy having from one to four carbon atoms, alkyl having from one to four carbon atoms, nitro and amino; wherein Heteroaryl is

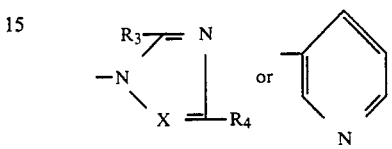

wherein $R_3$ and $R_4$ may be selected from hydrogen, alkyl having from one to four carbon atoms, or phenyl; and X is CH or N, together with the pharmaceutically acceptable salts thereof.

15. A thromboxane synthetase enzyme-inhibiting composition of matter in dosage unit form comprising from about 10 mg to about 70 mg of a compound selected from those of the formula:

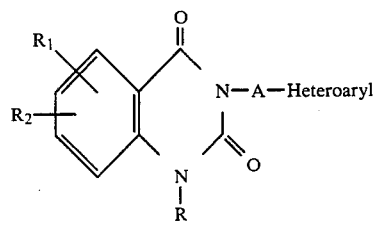

wherein A is a divalent moiety of the formula:

$-C_nH_{2n}-$  $-CH_2CH=CHCH_2-$ or $$-CH-CH_2CH_2-$$
$$\phantom{-}|\phantom{-}$$
$$\phantom{-}C_6H_5$$

wherein n is an integer from 2-10, inclusive; R is hydrogen or alkyl having from one to four carbon atoms; $R_1$ and $R_2$ may be the same or different and may be selected from the group consisting of hydrogen, halogen, trifluoromethyl, alkoxy having from one to four carbon atoms, alkyl having from one to four carbon atoms, nitro and amino; wherein Heteroaryl is

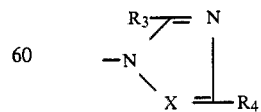

wherein $R_3$ and $R_4$ may be selected from hydrogen, alkyl having from one to four carbon atoms, or phenyl; and X is CH or N, together with the pharmaceutically acceptable salts thereof in association with a pharmaceutically acceptable carrier.

16. A method of lowering elevated blood pressure in a mammal which comprises administering internally to said mammal a pharmacologically effective amount of a compound selected from the group consisting of those of the formula:

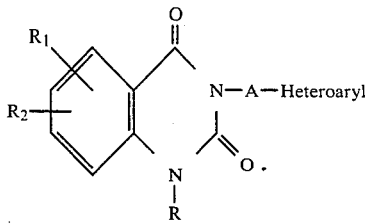

wherein A is a divalent moiety of the formula:

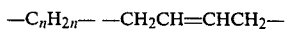

or

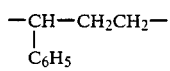

wherein n is an integer from 2–10, inclusive; R is hydrogen or alkyl having from one to four carbon atoms; $R_1$ and $R_2$ may be the same or different and may be selected from the group consisting of hydrogen, halogen, trifluoromethyl, alkoxy having from one to four carbon atoms, alkyl having from one to four carbon atoms, nitro and amino; wherein Heteroaryl is

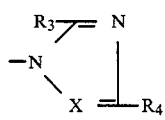

wherein $R_3$ and $R_4$ may be selected from hydrogen, alkyl having from one to four carbon atoms, or phenyl; and X is CH or N, together with the pharmaceutically acceptable salts thereof.

17. A therapeutic composition in dosage unit form useful for lowering elevated blood pressure in mammals comprising from about 10 mg to about 700 mg of a compound selected from the group consisting of those of the formula:

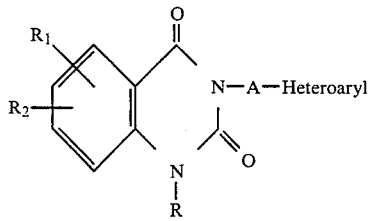

wherein A is a divalent moiety of the formula:

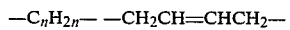

or

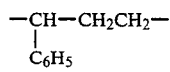

wherein n is an integer from 2–10, inclusive; R is hydrogen or alkyl having from one to four carbon atoms; $R_1$ and $R_2$ may be the same or different and may be selected from the group consisting of hydrogen, halogen, trifluoromethyl, alkoxy having from one to four carbon atoms, alkyl having from one to four carbon atoms, nitro and amino; wherein Heteroaryl is

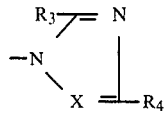

wherein $R_3$ and $R_4$ may be selected from hydrogen, alkyl having from one to four carbon atoms, or phenyl; and X is CH or N, together with the pharmaceutically acceptable salts thereof.

18. A method of treating diseases in a mammal characterized by an imbalance of thromboxane A$_2$/prostacyclin which comprises administering internally to said mammal a pharmacologically effective amount of a compound selected from the group consisting of those of the formula:

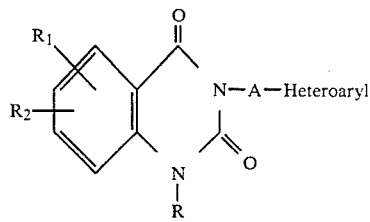

wherein A is a divalent moiety of the formula:

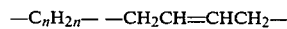

or

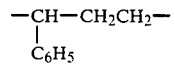

wherein n is an integer from 2–10, inclusive; R is hydrogen or alkyl having from one to four carbon atoms; $R_1$ and $R_2$ may be the same or different and may be selected from the group consisting of hydrogen, halogen, trifluoromethyl, alkoxy having from one to four carbon atoms, alkyl having from one to four carbon atoms, nitro and amino; wherein Heteroaryl is

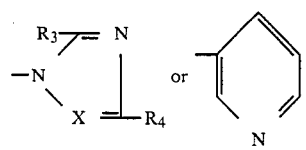

wherein $R_3$ and $R_4$ may be selected from hydrogen, alkyl having from one to four carbon atoms, or phenyl; and X is CH or N, together with the pharmaceutically acceptable salts thereof.

19. The method according to claim 18 wherein the disease is ischemic heart disease, transient ischemic attack, thrombosis or migraine.

20. A compound according to claim 1, which is 6-chloro-3-[3-(1H-imididazol-1-yl)-2-methylpropyl]-2,4-(1H,3H)-quinazolinedione; 7-chloro-3-[3-1H-imidazol-1-yl)-2-methylpropyl]-2,4(1H,3H)-quinazolinedione; or the monohydrochloride salt of either of the above.

* * * * *

UNITED STATES PATENT OFFICE
CERTIFICATE OF CORRECTION

Patent No. 4,684,654  Dated August 4, 1987

Inventor(s) WILLIAM B. WRIGHT, JR and ANDREW S. TOMCUFCIK

It is certified that error appears in the above-identified patent and that said Letters Patent are hereby corrected as shown below:

IN THE TITLE: QUINZAOLINED- should read QUINAZOLINED-

IN THE ABSTRACT: Line 14, delete t,0012 and replace with the following formula:

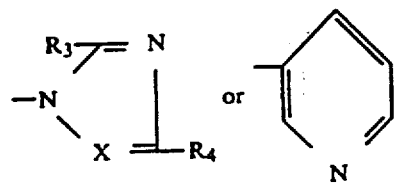

UNITED STATES PATENT OFFICE
CERTIFICATE OF CORRECTION

Patent No. 4,684,654      Dated August 4, 1987

Inventor(s) WILLIAM B. WRIGHT, JR and ANDREW S. TOMCUFCIK

It is certified that error appears in the above-identified patent and that said Letters Patent are hereby corrected as shown below:

Column 2, Line 40, Delete (3)↓ ETOCO1 Replace with (3)↓ ETOCOCl

Column 15, Last Line cancel "or"

Signed and Sealed this

Fifth Day of April, 1988

Attest:

DONALD J. QUIGG

Attesting Officer

Commissioner of Patents and Trademarks